United States Patent [19]

Mandell et al.

[11] 4,456,749

[45] Jun. 26, 1984

[54] PROCEDURE FOR PRECIPITATING CELLULOSE DERIVATIVE

[75] Inventors: Leo Mandell; Vidar Eklund; Kurt Ekman; Jouko Huttunen; Olli Turunen, all of Porvoo, Finland

[73] Assignee: Neste Oy, Finland

[21] Appl. No.: 537,370

[22] PCT Filed: Dec. 30, 1982

[86] PCT No.: PCT/FI82/00070

§ 371 Date: Aug. 30, 1983

§ 102(e) Date: Aug. 30, 1983

[87] PCT Pub. No.: WO83/02279

PCT Pub. Date: Jul. 7, 1983

[30] Foreign Application Priority Data

Dec. 30, 1981 [FI] Finland .................... 814209

[51] Int. Cl.$^3$ ................ C08B 15/06; C08B 3/28; C08B 11/22
[52] U.S. Cl. ................. 536/30; 264/178 R; 264/178 F; 264/187
[58] Field of Search .......... 536/30; 264/178 R, 178 F, 264/187

[56] References Cited

U.S. PATENT DOCUMENTS

| 2,129,708 | 9/1938 | Schreiber | 536/30 |
| 2,134,825 | 11/1938 | Hill et al. | 536/30 |
| 4,367,191 | 1/1983 | Cuculo et al. | 264/187 |
| 4,404,369 | 9/1983 | Huttunen et al. | 536/30 |

FOREIGN PATENT DOCUMENTS

| 57105 | 8/1982 | European Pat. Off. | 536/30 |
| 61033 | 10/1979 | Finland . | |
| 216475 | 11/1924 | United Kingdom | 536/30 |
| 516672 | 1/1940 | United Kingdom | 536/30 |
| 1265010 | 3/1972 | United Kingdom | 536/30 |

*Primary Examiner*—Ronald W. Griffin
*Attorney, Agent, or Firm*—Steinberg & Raskin

[57] ABSTRACT

The present invention concerns a procedure for precipitating cellulose carbamate from an aqueous alkali solution. The solution is brought into contact with an aqueous solution of sulphuric acid containing one or several cations selected from the group consisting of Na, Al, Mg, Zn and Ca cations, whereby in the precipitation of cellulose carbamate the advantage is gained that the dry matter content of the fibre can be made high enough.

4 Claims, No Drawings

PROCEDURE FOR PRECIPITATING CELLULOSE DERIVATIVE

The present invention concerns a procedure for precipitating a cellulose derivative from an alkali solution. In particular the invention relates to a procedure for precipitating cellulose carbamate from its alkali solution, in the form of fibre or film.

In the Finnish patent application Nos. 793226 and 810226 is disclosed a procedure for producing an alkali soluble cellulose derivative from cellulose and urea at elevated temperature. The procedure is based on the fact that when urea is heated to its melting point or to a higher temperature it begins to decompose into isocyanic acid and ammonia. Isocyanic acid in itself is no particularly stable compound: it tends to become trimerized into isocyanuric acid. Further, isocyanic acid tends to react with urea, whereby biuret is formed. Isocyanic acid also reacts with cellulose, producing an alkali soluble cellulose compound which is called cellulose carbamate. The reaction may be written as follows:

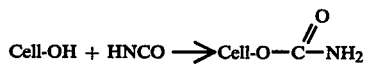

The compound thus produced, cellulose carbamate, may be dried after washing and stored even over prolonged periods, or it may be dissolved in an aqueous alkali solution, for manufacturing fibre for instance. From this solution may be manufactured cellulose carbamate fibres or films by spinning or by extruding, in like manner as in the viscose manufacturing process. The keeping quality and transportability of cellulose carbamate in dry state afford a great advantage compared with the cellulose xanthate in the viscose process, which cannot be stored nor transported, not even in solution form.

If, for instance, continuous fibre or filament manufactured from cellulose carbamate suitable for textile use is required, it is necessary first to make a solution of carbamate in an aqueous solution of alkali, e.g. of sodium hydroxide. Thereafter, it is possible to precipitate from this solution fibre or film in like manner as in manufacturing viscose fibre cellulose is regenerated from a NaOH solution of cellulose xanthate. In the viscose process, xanthate solution is as a rule spun into a precipitation bath which contains dilute sulphuric acid and sodium sulphate.

Although the precipitation of cellulose carbamate in sulphuric acid resembles the precipitation process in the viscose method, it is a totally different matter in principle. Cellulose carbamate is stable in acid conditions and does not, therefore, decompose into cellulose on precipitating, as in the viscose process. However, contacting the alkaline solution of the carbamate with sulphuric acid induces precipitation of the cellulose carbamate, and at the same time sodium sulphate is formed as sodium hydroxide is neutralized.

When trying to apply, in the precipitation of cellulose carbamate from a solution of sodium hydroxide, similar precipitation solutions to those used in manufacturing viscose, it was found that the dry matter content of the precipitated carbamate fibre remained for lower than in the viscose process, which is far too low. This has the further consequence that the initial strength of the fibre product thus produced was not sufficent to tolerate the mechanical stresses involved in the treatment of the fibre. The low dry matter content of the fibre also implies that in the drying phase of the fibre much more water must be evaporated and more energy consumed.

The object of the present invention is a procedure in which in the precipitation of cellulose carbamate a high enough dry matter content is achieved. The procedure of the invention for precipitating cellulose carbamate from an alkali solution is characterized in that the solution is brought into contact with an aqueous solution of sulphuric acid containing one or several cations selected from the group: Na, Al, Mg, Zn and Ca cations.

Suitable sources for supplying Al, Mg, Ca or Zn cations are the corresponding sulphates, although also other salts, for instance chlorides, may be used. Differences exist between different cations: it appears as if trivalent cations were more powerful than bivalent or monovalent cations. A highly advisable cation source is aluminium sulphate, but results have also been attained with magnesium sulphate, sodium aluminium sulphate—or alum—and with zinc sulphate. Calcium sulphate may also be used, although its solubility in dilute sulphuric acid is fairly low.

As in the viscose process, it is likewise possible to regulate and control the precipitation circumstances of cellulose carbamate by changing the process conditions. Such process variables are e.g. the composition of the precipitation bath, temperature, time, carbamate content of the solution, its viscosity, etc. The sulphuric acid content affects e.g. the carbamate precipitation rate, while the cation content affects the dry matter content of the fibre in the first place. The proper sulphuric acid content in the procedure of the invention varies as a rule between 2–20% by weight and the quantity of Al, Mg, Ca or Zn salt between 0.1–25% by weight. In a continuous process, sodium sulphate accumulates in the solution, and the precipitation solution may therefore be regenerated as known in the art by adding substances consumed during the process and removing substances which accumulate in excess quantities. It is thus possible in the process of the invention to remove sodium sulphate e.g. by evaporating water and precipitating, and to add sulphuric acid and aluminium sulphate or another sulphate. The quantity of sodium sulphate is normally kept between 3 and 30% by weight.

By the procedure of the invention both fibres and films can be produced using conventional apparatus and processes of the viscose method. When fibres are produced, the carbamate solution is spun through spinning orifices into the precipitation bath, and when films are produced, the solution is pressed through a slit orifice to become film.

In the procedure of the invention, the sodium hydroxide solution of cellulose carbamate contains 4–15% by weight of cellulose carbamate. A proper viscosity for the solution is as a rule between 50 and 500 P.

After precipitation, the after-treatment of the fibres or films such as washing, drying etc. steps may be carried out using methods and apparatus known in themselves in the art and which do not fall within the scope of the present invention.

In the examples attached, an application of the invention is illustrated in the spinning of cellulose carbamate fibres, while it is obvious that the method of the invention is not confined only to precipitating fibre but it is equally suitable for manufacturing film-like products on other kinds of products by precipitating cellulose carbamate from an alkali solution.

EXAMPLE 1

Cellulose carbamate was made by mixing 430 g of dry-beaten bleached pine cellulose (DP 510) and 35 g of $Na_2CO_3$ in cold xylene in a glass flask with reflux condenser. The xylene was warmed to 139° C., and 500 g of granular urea was added. Warming with agitation was continued for two hours. Thereafter, the xylene was distilled off in subatmospheric pressure, and the cellulose carbamate product was washed with water. The nitrogen content of the carbamate was 3.6% by weight and DP was 365.

A cellulose carbamate solution was prepared by dissolving cellulose carbamate produced in the manner just described in a 10% NaOH solution. The carbamate content of the solution was 5.8% and the ball viscosity, 53 s.

The clogging number of the solution was determined by the method described in: H. Sihtola, Paperi ja Puu 44 (1962), No. 5, p. 295–300. The clogging number of the solution was found to be 15,000. The solution was pressed into a sulphuric acid solution through an orifice with 100 holes of 0.09 mm diameter.

The fibre strand produced by precipitation in the sulphuric acid solution was lifted onto a roll from the precipitation solution. The dry matter content of the fibres was determined in two ways. In one case, the fibre strand was first dried between blotting cardboards. Thereafter, the fibres were weighed, washed with water and once again weighed, and the dry matter content was calculated. In the other case, the fibres were not dried between blotting papers before the first weighing.

In Table I have have been stated the compositions of the precipitation solutions used, the precipitation times and the dry matter contents obtained.

TABLE I

| Composition of precipitation solutions | Precipitation time(s) | Dry matter content dried (% by w.) | Dry matter content not dried (% by w.) |
|---|---|---|---|
| 6% $H_2SO_4$ | 16 | 9.6 | 5.6 |
| 12% $H_2SO_4$ | 16 | 9.9 | 5.6 |
| 10% $H_2SO_4$ + 7% $Na_2SO_4$ | 16 | 8.9 | 5.2 |
| 12% $H_2SO_4$ + 18% $Na_2SO_4$ | 20 | 10.3 | 5.1 |
| 12% $H_2SO_4$ + 30% $Na_2SO_4$ | 20 | 8.7 | 5.5 |
| 20% $H_2SO_4$ + 30% $Na_2SO_4$ | 20 | 8.8 | 4.6 |
| 10% $H_2SO_4$ + 10% $Al_2(SO_4)_3$ | 16 | 13.4 | 10.1 |
| 10% $H_2SO_4$ + 15% $Al_2(SO_4)_3$ | 16 | 19.7 | 13.4 |
| 10% $H_2SO_4$ + 10% $Al_2(SO_4)_3$ + 15% $Na_2SO_4$ | 16 | 17.1 | 12.2 |
| 10% $H_2SO_4$ + 10% $Al_2(SO_4)_3$ + 15% $Na_2SO_4$ | 8 | 16.8 | 11.7 |

This example shows that cellulose carbamate is precipitated even in mere sulphuric acid solution, but that the dry matter content remains low. In the same way behaves a precipitating solution containing sodium sulphate in addition to sulphuric acid. Aluminium sulphate causes a substantial improvement in the dry matter content of the fibre.

EXAMPLE 2

Cellulose carbamate was manufactured as follows: 430 g dry-dispersed bleached sulphite cellulose (spruce/pine) (DP 400) was impregnated with a solution containing 3.6 l of liquid ammonia and 200 g of urea, at −45° C. for 3 hrs. Thereafter, the ammonia was allowed to evaporate at room temperature in a 15 liter reactor overnight. The reactor temperature was raised to be 135° C. for three hours, whereafter the cellulose carbamate product (with N content 2.4%, DP 310) was washed with water and dissolved in 10% NaOH solution. The carbamate content of the solution was 6.5% by weight and the clogging number, 13,000.

Precipitation tests were carried out in the manner of Example 1, but using zinc and magnesium cations. The results are stated in Table II.

TABLE II

| Composition of precipitation solutions | Precipitation time(s) | Dry matter content dried (% by w.) | Dry matter content not dried (% by w.) |
|---|---|---|---|
| 10% $H_2SO_4$ + 5% $MgSO_4$ | 16 | 13.2 | — |
| 10% $H_2SO_4$ + 10% $MgSO_4$ | 6 | 10.8 | — |
| 10% $H_2SO_4$ + 5% $ZnSO_4$ | 6 | 10.4 | 5.5 |
| 10% $H_2SO_4$ + 5% $ZnSO_4$ + 15% $Na_2SO_4$ | 1 | 9.9 | 5.7 |
| 10% $H_2SO_4$ + 5% $ZnSO_4$ + 25% $Na_2SO_4$ | 1 | 10.7 | 5.4 |
| 9% $H_2SO_4$ + 9% $ZnSO_4$ + 18% $Na_2SO_4$ | 1 | 9.2 | 5.3 |

EXAMPLE 3

Cellulose carbamate was manufactured as in Example 2, with the exception that the urea quantity was 300 g. The DP of the cellulose carbamate thus obtained was 320 and the nitrogen content, 2,2%.

A solution was prepared of the cellulose carbamate as in Example 2. The carbamate content of the solution was 6.5% by weight and the clogging number was 1045. The results of the precipitation tests are stated in Table III.

TABLE III

| Composition of precipitation solutions | Precipitation time(s) | Dry matter content dried (% by w.) | Dry matter content not dried (% by w.) |
|---|---|---|---|
| 5% $H_2SO_4$ + 15% $Al_2(SO_4)_3$ | 16 | 14.7 | 10.0 |
| 10% $H_2SO_4$ + 15% $Al_2(SO_4)_3$ | 16 | 20.0 | — |
| 15% $H_2SO_4$ + 15% $Al_2(SO_4)_3$ | 16 | 14.2 | 10.9 |

EXAMPLE 4

Cellulose carbamate was made as in Example 3, with the exception that bleached sulphite cellulose (pine) was used as the starting material, the DP of which was 380. The nitrogen content of the carbamate was 1.7% and its DP, 290. A NaOH solution was made from the carbamate as in Example 3, and the clogging number was found to be 1900. The precipitation solutions that were used are stated in Table IV. The precipitation time was 11 minutes.

TABLE IV

| Composition of precipitation solutions | Dry matter content dried (% by w.) | not dried (% by w.) |
|---|---|---|
| 10% $H_2SO_4$ + 5% $Al_2(SO_4)_3$ + 20% $Na_2SO_4$ | 12.7 | 9.9 |
| 10% $H_2SO_4$ + 5% $Al_2(SO_4)_3$ + 25% $Na_2SO_4$ | 17.0 | 11.9 |
| 10% $H_2SO_4$ + 7% $Al_2(SO_4)_3$ + 20% $Na_2SO_4$ | 18.5 | 12.0 |
| 10% $H_2SO_4$ + 5% $NaAl(SO_4)_2$ | 17.1 | 12.6 |

We claim:

1. Procedure for precipitating cellulose carbamate from an aqueous alkali solution, characterized in that the solution is brought into contact with an aqueous solution of sulphuric acid containing one or several cations selected from the group consisting of Na, Al, Mg, Zn and Ca cations.

2. Procedure according to claim 1, characterized in that the sulphuric acid solution contains 2-20 % by weight sulphuric acid, 3-30% by weight sodium sulphate and 0.1-25% by weight aluminium, magnesium, calcium or zinc sulphate.

3. Procedure according to claim 1, characterized in that the alkali solution of the carbamate is pressed through a perforated or slit-like orifice into the sulphuric acid solution to the purpose of precipitating carbamate fibre or film.

4. Procedure according to any one of claims 1, characterized in that the alkali solution of carbamate contains 4-15% by weight of cellulose carbamate.

* * * * *